(12) United States Patent
Woo et al.

(10) Patent No.: US 10,335,587 B2
(45) Date of Patent: Jul. 2, 2019

(54) WEARABLE BAND FOR LOW-FREQUENCY THERAPY

(71) Applicants: Dae-Ki Woo, Seongnam-si (KR); Byong-No Woo, Seongnam-si (KR)

(72) Inventors: Dae-Ki Woo, Seongnam-si (KR); Byong-No Woo, Seongnam-si (KR)

(*) Notice: Subject to any disclaimer, the term of this patent is extended or adjusted under 35 U.S.C. 154(b) by 64 days.

(21) Appl. No.: 15/534,490

(22) PCT Filed: Dec. 10, 2015

(86) PCT No.: PCT/KR2015/013490
§ 371 (c)(1),
(2) Date: Jun. 9, 2017

(87) PCT Pub. No.: WO2016/093632
PCT Pub. Date: Jun. 16, 2016

(65) Prior Publication Data
US 2017/0319844 A1 Nov. 9, 2017

(30) Foreign Application Priority Data

Dec. 12, 2014 (KR) .................. 10-2014-0179529
Dec. 16, 2014 (KR) .................. 10-2014-0181359
Jul. 13, 2015 (KR) .................. 10-2015-0099055

(51) Int. Cl.
*A61N 1/04* (2006.01)
*A61N 1/32* (2006.01)
*A61N 1/36* (2006.01)

(52) U.S. Cl.
CPC ............. *A61N 1/0472* (2013.01); *A61N 1/04* (2013.01); *A61N 1/0452* (2013.01);
(Continued)

(58) Field of Classification Search
CPC .. A61N 1/0484; A61N 1/0452; A61N 1/0456; A61N 1/36; A61N 1/321
See application file for complete search history.

(56) References Cited

U.S. PATENT DOCUMENTS

2005/0203586 A1* 9/2005 Yu .................. A61H 39/002
607/46
2005/0205551 A1* 9/2005 Aisenbrey ........... B29C 45/0013
219/529
(Continued)

FOREIGN PATENT DOCUMENTS

JP     2005-349021     12/2005
KR     20-0313130     5/2003
(Continued)

OTHER PUBLICATIONS

English abstract of JP2005-349021.
(Continued)

*Primary Examiner* — Eric D. Bertram
(74) *Attorney, Agent, or Firm* — Antonio Ha & U.S. Patent, LLC (57) ABSTRACT

The present invention relates to a wearable band for low frequency therapy and, more specifically, to a wearable band for low frequency therapy, the wearable band enabling a wearer to connect to a low frequency therapy device while wearing, on a body part, a cylindrical wearable band in which knitted pile yarn is formed from conductive fiber, thereby providing low-frequency stimulation to the part of the wearer's body such that the wearer can receive physical therapy.

8 Claims, 10 Drawing Sheets

(52) U.S. Cl.
CPC ......... *A61N 1/0456* (2013.01); *A61N 1/0484* (2013.01); *A61N 1/32* (2013.01); *A61N 1/322* (2013.01); *A61N 1/36* (2013.01); *A61N 1/36014* (2013.01); *A61N 1/321* (2013.01); *A61N 1/36003* (2013.01)

(56) References Cited

U.S. PATENT DOCUMENTS

| | | | | |
|---|---|---|---|---|
| 2007/0010750 | A1* | 1/2007 | Ueno | A61B 5/0408 600/509 |
| 2007/0282409 | A1* | 12/2007 | Lee | A61N 1/0408 607/115 |
| 2010/0317954 | A1* | 12/2010 | Jeong | A61B 5/04085 600/372 |
| 2013/0102217 | A1* | 4/2013 | Jeon | D03D 15/0027 442/182 |
| 2017/0333706 | A1* | 11/2017 | Schepis | A61N 1/0476 |

FOREIGN PATENT DOCUMENTS

| | | |
|---|---|---|
| KR | 10-2005-0098615 | 10/2005 |
| KR | 20-0427531 | 9/2006 |
| KR | 10-2012-0023161 | 3/2012 |
| KR | 20-0464005 | 12/2012 |
| WO | 2009-145536 | 12/2009 |

OTHER PUBLICATIONS

English translation of KR20-0313130.
English translation of KR10-2012-0023161.
English translation of KR10-2005-0098615.
English abstract of WO2009-145536.
English translation of KR20-0427531.
English translation of KR20-0464005.

* cited by examiner

WEARABLE BAND FOR LOW-FREQUENCY THERAPY

TECHNICAL FIELD

The present invention relates to a wearable band for low-frequency therapy, and more specifically, to a low-frequency therapy wearing band that includes knitted pile yarn formed of a conductive fiber, is shaped as a cylinder, and is connected to a low-frequency therapy device while being put on a body part, applying low-frequency stimulation to the body part to enable physical therapy.

DISCUSSION OF RELATED ART

Generally, low-frequency therapy devices are therapeutic machines that apply low-frequency pulses to human bodies to physically massage nerves or muscles.

A low-frequency therapy device includes a control box constituted of a case, a power supply, a controller, a low-frequency wave output unit, a control switch, and electrodes. Conductive rub pads of the electrodes having negative, and positive polarities are wired to the control box to apply low-frequency stimuli, enabling physical therapy.

The rubber electrode pads, which are attached to a human body, have a limited area of attachment, rendering it difficult to increase the area of contact to the pads. Thus, the effect of physical treatment is limited. Further, the electrodes, which consist of adhesive pads, may lose the effect of high-frequency stimulation as the surface of attachment is contaminated after it is used about 30 to about 50 times, and a failure to tightly contact the skin may cause stinging or other inconvenient feelings:

There have conventionally been proposed a "multi-functional low-frequency physical therapeutic device having protrusions for stimulating acupuncture points" disclosed in Korean Utility Model Registration No. 20-0427531 thereinafter, prior reference 1 and a "low-frequency physical therapeutic device" disclosed in Korean Utility Model Registration No. 20-0464005 (hereinafter, prior reference 2).

Prior reference 1 discloses an electrical massaging device that applies positive and negative low-frequency electrical stimuli from a low-frequency generator to a flexible and soft fabric body and includes a pad-type massaging body, the fabric body formed of a carbon-containing conductive rubber that allows the fabric body to have flexibility and more stability in shape, and multiple acupressure protrusions for stimulating acupuncture points which are evenly arranged on the surface directly contacting the skin, enhancing metabolism and blood circulation in the body through the synergy of the acupuncture of oriental medicine and electrical stimulation.

Prior reference 2 discloses a low-frequency physical therapeutic device that includes a band-shaped body, multiple tourmanium ceramics to generate far-infrared radiations and negative ions, multiple conducting rubbers arranged away from a surface of the body at a predetermined interval to be positioned between the tourmanium ceramics and having different working cycles and working times, and a controller installed in the body to control the magnitude of a current supplied to the conducting rubbers and the time of the supply of the current and having a current supplying means. The conducting rubbers, respectively, include a pair of protruding pins that pass through the body and are bent so that the conducting rubbers are fastened to the body. The conducting rubbers are projected higher than the to ceramics. The tourmanium ceramics each are shaped as a rectangular parallelepiped having a trapezoidal cross section to prevent damages to the edges.

The band-shaped structures disclosed in prior references 1 and 2 results in a failure to increase the area, massaged and inconvenience in wearing. Moreover, the acupressure protrusions and protruding electrodes arranged on conductive rubbers contacting the skin render the structures more complicated, leading to a cost rise and trickier manufacturing process.

SUMMARY

The present invention has been conceived to address the above-mentioned problems, and an object of the present invention is to provide a wearable band for low frequency therapy enabling a wearer to connect to a low frequency therapy device while wearing, on a body part, a cylindrical wearable band in which knitted pile yarn is formed from conductive fiber, thereby providing low-frequency stimulation to the part of the wearer's body such that the wearer can receive physical therapy.

To achieve the above object, according to the present invention, a low-frequency therapy wearing band allowing a low-frequency therapy device including a control box constituted of a case, a power supply, a controller, a low-frequency wave output unit, and a control switch to be connected thereto to provide a low-frequency stimulus to a body part of a wearer to enable physical therapy comprises outer yarn shaped as a cylinder by continuously knitting fiber yarn loops and knitted with fiber, inner yarn knitted with covering yarn, and pile yarn formed of a conductive fiber, knitted at inner surfaces of the inner yarn, and applying a low-frequency stimulus while tightly contacting a skin, wherein a cable of the low-frequency therapy device is connected to electrode terminals protruding from a surface to transmit a negative low-frequency current and a positive low-frequency current to the pile yarn.

As described above, according to the present invention, the low-frequency therapy wearing band is formed of a fiber material, easy to wear on a body part, prevents static electricity when worn, and comes in tight contact with the skin by the elasticity of the wearing band. Therefore, physical therapy may flexibly be conducted on a broad area of human body, maximizing the therapeutic effects.

10: low-frequency therapy device
11: control box
12: power supply
13: controller
14: low-frequency output unit
15: control switch
16: cable
20: tearing band
21: outer yarn
22: inner yarn
221: copper yarn 222: coat yarn
23: pile yarn
24: electrode terminal
25: elastic hand
30: stainless fiber

DETAILED DESCRIPTION OF EXEMPLARY EMBODIMENTS

Hereinafter, preferred embodiments of the present invention are described with reference to the accompanying drawings.

Figure 1:
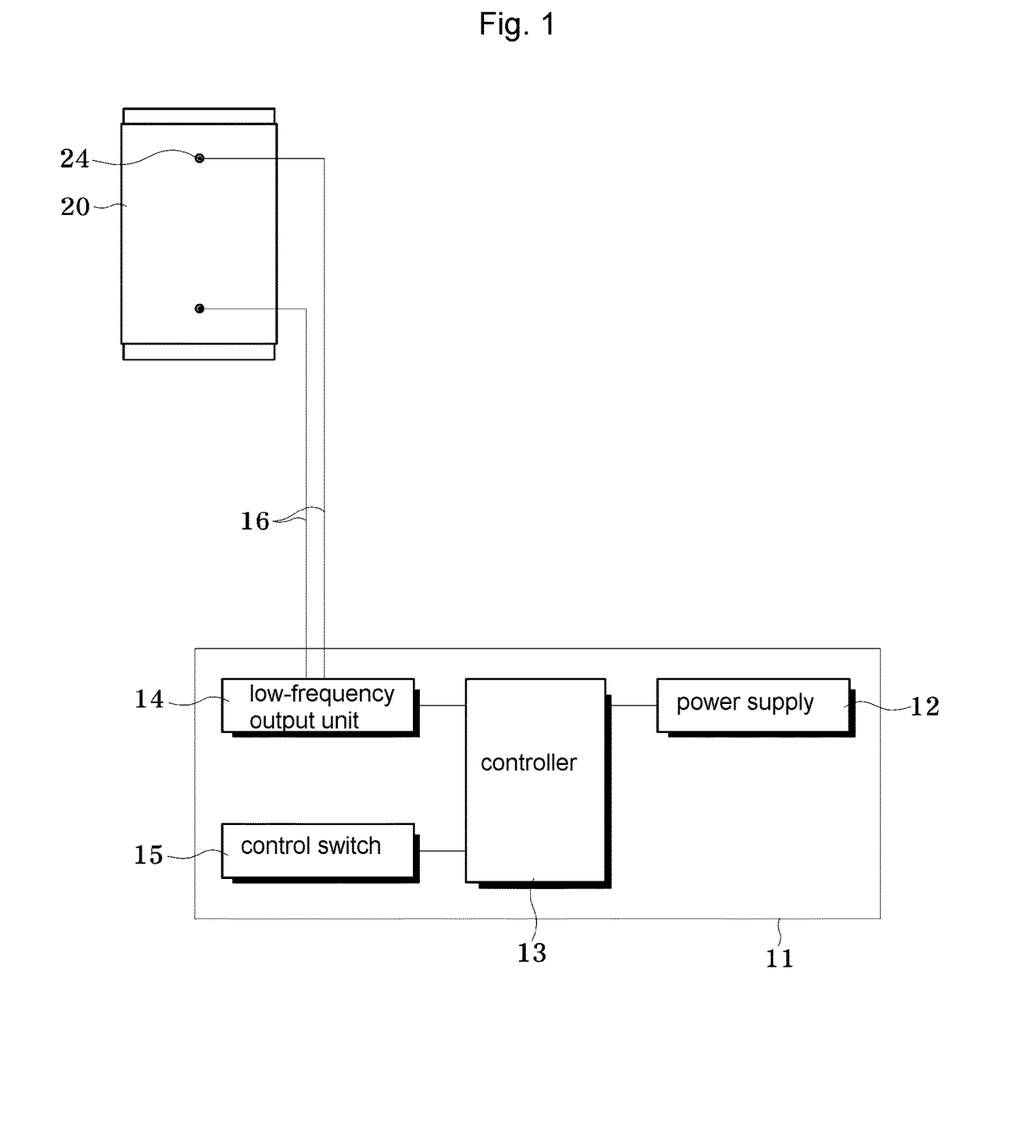
FIG. 1 is a block diagram illustrating a configuration of a low-frequency therapy device and a low-frequency therapy wearing band according to the present invention.

Referring to FIG. 1, according to the present invention, a low-frequency therapy wearing band 20 is connected to a low-frequency therapy device 10 that includes a control box 11, a power supply 12, a controller 13, a low-frequency output unit 14, and a control switch 15 which are configured in a casing. The low-frequency therapy wearing band 20 is attached to a wearer's body portion to apply, a low-frequency stimulus to the both portion to enable physical therapy.

The low-frequency therapy device 10 falls within a well-known technology. According to the present intention, a wearing band 20 for low-frequency therapy may be easy to wear, tightly contact the ski, and increase an area of contact to the human both to enable efficient physical therapy.

Figure 2:
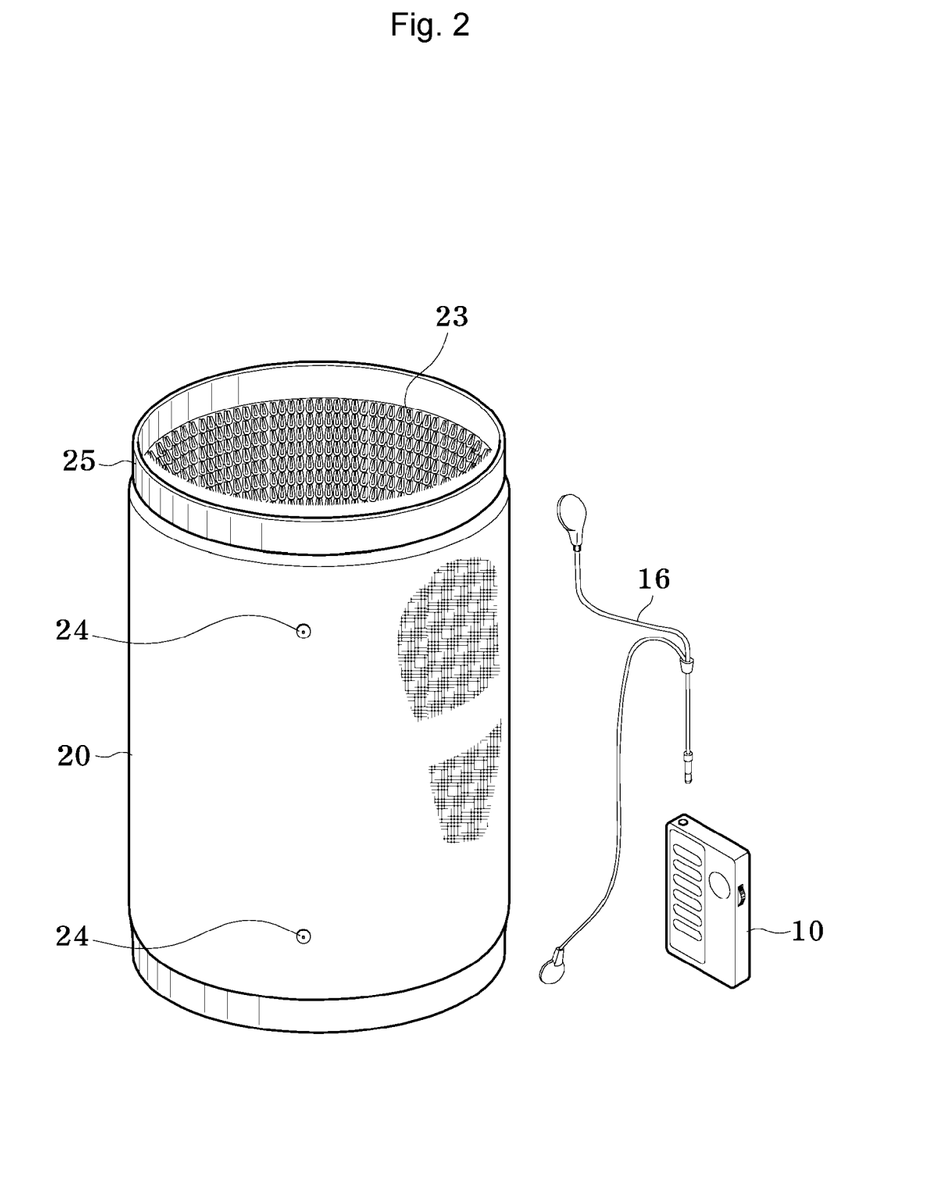
FIG. 2 is a perspective view illustrating a low-frequency therapy wearing band according to the present invention.
Figure 3:
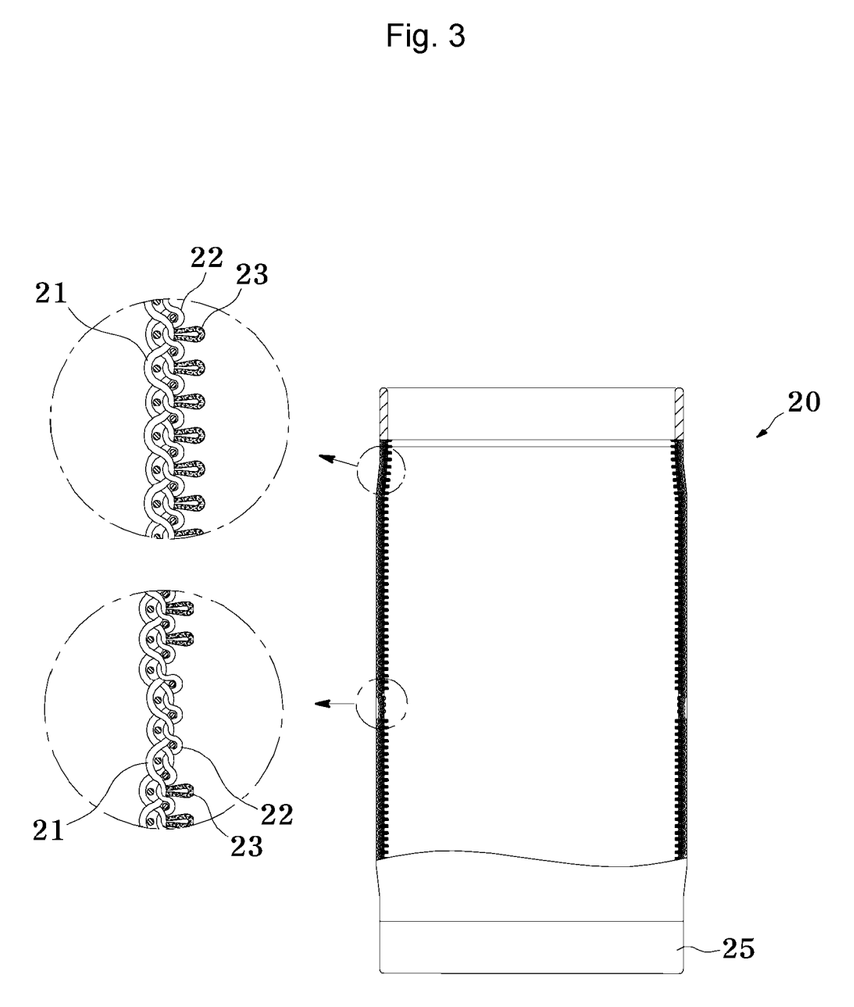
FIG. 3 is a cross-sectional view illustrating a low-frequency therapy wearing band according, to the present invention.

Referring to FIGS. 2 and 3, the wearing band 20 includes electrode terminals 24 that are protruded from a surface of the wearing band 20 and connected with cables 16 of the low-frequency therapy 10 to transfer negative and positive low-frequency currents to pile yarn 23.

In particular, the wearing band 20 has elastic bands 25 at upper and lower parts thereof. The elastic bands 25 are formed by knitting rubber yarn along with synthetic fibers, thus providing significant elasticity. Therefore, the upper and lower parts of the wearing band 20 may be squeezed by the elastic band s25, allowing them to tightly contact an area of use.

In the wearing band 20, the pile yarn 23 is formed to be divided into upper pile yarn and lower pile tread inside the wearing band 20, so that a positive current flows through the upper pile yarn and a negative current flows through the lower pile yarn. In addition to the elastic bands 25 formed at the upper and lower parts of the wearing band 20, an elastic band 25 may also be formed between the upper and lower parts of the wearing band 20.

The electrode terminals 24 electrically connected with the pile, yarn 23 are protruded from an upper and lower part, respectively, of the wearing hand 20. The electrode terminals 24 are connected with the tow-frequency therapy device 10 to apply a negative low-frequency current and a positive low-frequency current to the upper and lower pile yarn 23, respectively.

Figure 4:
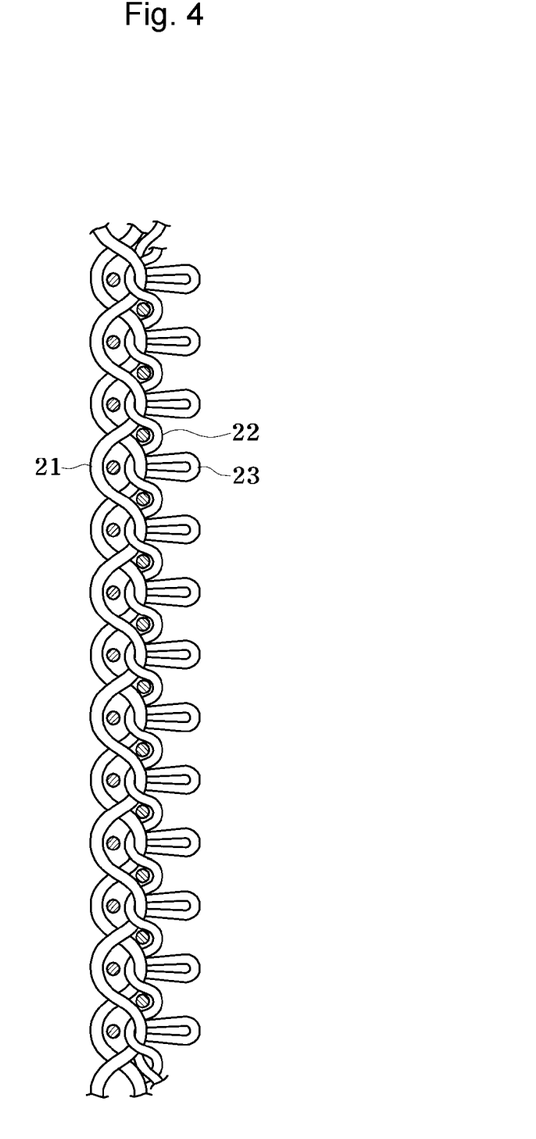
FIG. 4 is an expanded cross-sectional view illustrating a low-frequency therapy wearing band according to the present invention.

As illustrated in FIG. 4, the wearing band 20 is formed to have a cylindrical shape as needles mounted in a cylindrical needle cylinder of a knitting machine continuously knit fiber yarn into loops, and the wearing hand 20 includes outer yarn 21 knitted with fiber yarn, inner yarn 22 knitted with covering yarn, and the pile yarn 23 formed of conducting fiber, knitted at inner surfaces of the inner yarn 22 and tightly contacting the skin to apply a tow-frequency stimulus to the skin.

Figure 5:
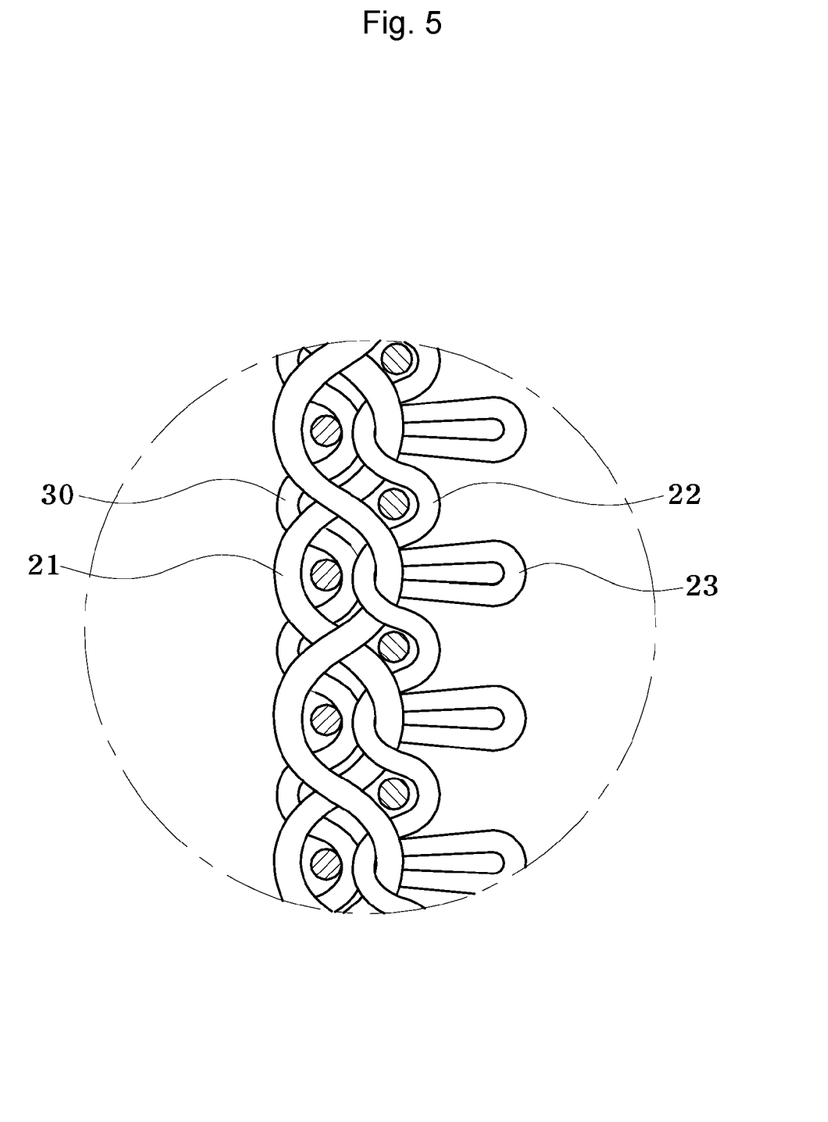
FIG. 5 is a view illustrating another example of a low-frequency therapy wearing band according to the present invention.

Referring to FIG. 5, stainless fibers 30 are knitted at the outside of the outer yarn 21 to prevent static electricity that occurs due to a contact to the wearing band 20. Normal conducting fibers may be used instead of stainless fibers 30.

In other words, additionally knitting the stainless fibers 30 at the outside of the outer yarn 21, which are positioned at the outermost side of the wearing band may previously prevent static electricity and resultant electrical shocks that may occur when the wearing band is worn or removed.

Figure 6:
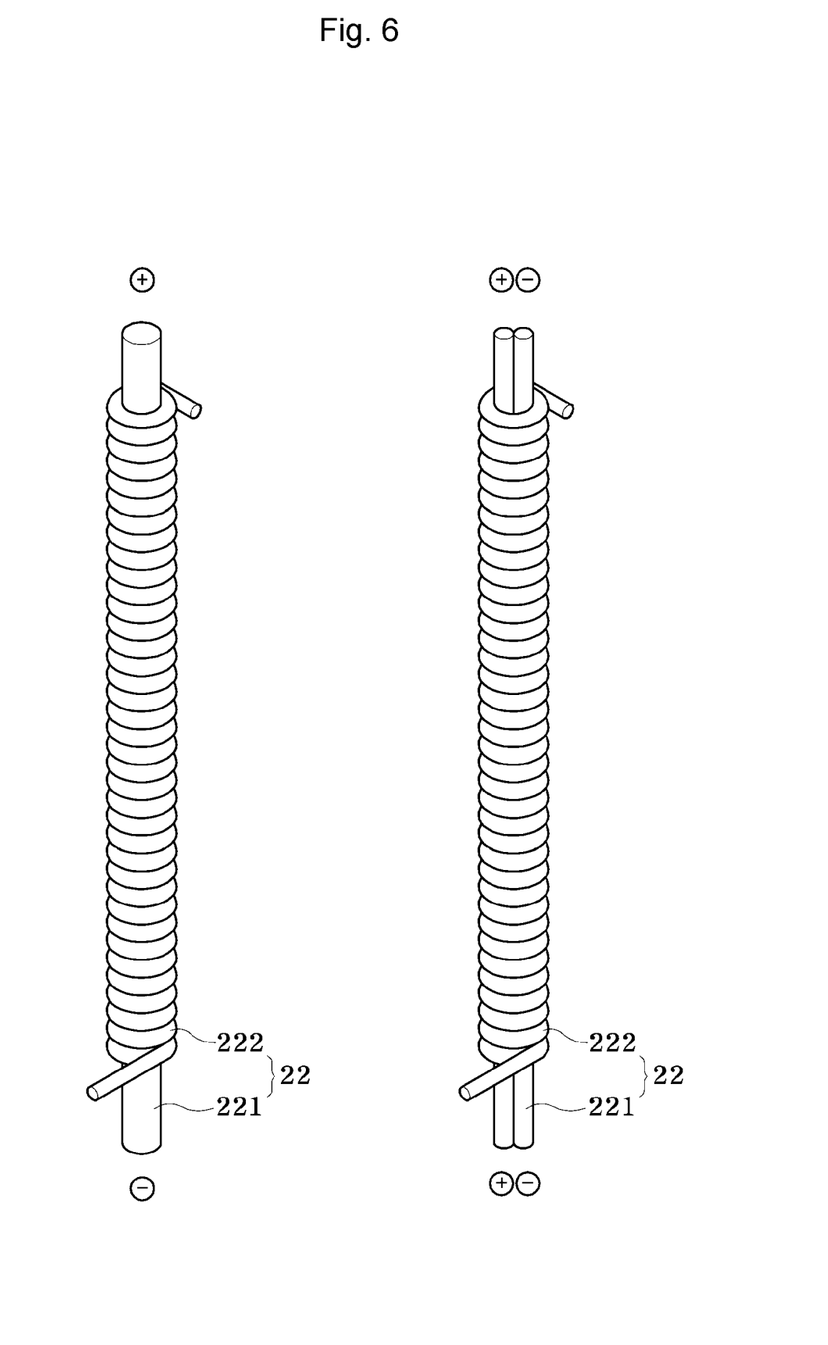
FIG. 6 is a perspective view illustrating inner yarn of a low-frequency therapy wearing band according to the present invention.

Referring to FIG. 6, the inner yarn includes metallic copper yarn 221 as a core and coat yarn 222 formed of elastic nylon or polyester and wo nd around the copper yarn 221. The cables 16 of the low-frequency therapy device 10 are connected to the electrode terminals 24 of the wearing band 20 so that the copper yarn 221 receives a current and is thus heated.

In particular, one or more pieces of copper yarn 221 may be used. Where one piece of copper yarn 221 is used, the copper yarn 221 is connected so that a positive current is applied to a side of the copper yarn 21 and a negative current applied to an opposite side of the copper yarn 221. Where more than one piece of copper yarn 221 are used, the copper yarn 221 are preferably connected so that both a positive and negative current may be applied to each of the two sides of the copper yarn 221.

As such, a physical therapy is performed by to low-frequency simulation with the wearing band 20 worn, the copper yarn 221 covered by the coat yarn 222 is heated to provide the effect of thermotherapy, leading to a better massage effect and enhancing the effect of the physical therapy.

The inner yarn may be knitted in the form of a mesh to show the effect of the knitting of the pile yarn, so that the inner yarn 222 has better air permeability and conductivity.

The inner yarn 22 is rubbed by an brush to raise a nap on the surface of the inner yarn 22. The nap fills the pile yarn and spaces among the pile yarn, leading to enhanced conductivity.

Preferably, a Teflon resin is coated oar the outside of the outside of the coat yarn 222 to prevent direct contact e wearer's skin, allowing for ready use by wearers who are sensitive to electrical stimulation or suffer from an itch due to frequent contacts.

Meanwhile, the pile yarn 23 forms a cloth in which myriad ring-shaped fiber hairs are embedded inside the inner yarn 22 when knitting the outer yarn 21 and the inner yarn 22, allowing the thickness to be freely adjusted while providing a soft feeling.

Preferably, the pile yarn 23 is formed of any one of a conductive fiber that is rendered to have conductivity by having an acrylic fiber react with copper sulfate, a conductive fiber obtained by mixing a fiber with carbon black, which is a conductive material, and a conductive fiber that is rendered to have conductivity by depositing a metal on the surface of a fiber.

In some cases, a raw material obtained by mixing 2 weight % to 6 weight % of copper powder with a high-molecular polymer that, constitutes a base material of the pile yarn 23 is melt-spun through 40-denier spinning holes, producing filament finished yarn. The filament finished yarn may be used, as the pile yarn 23.

As described above, forming the pile yarn 23 of a conductive fiber containing copper or a copper-like metal may remove static electricity that may occur from the synthetic fiber and enhance the wearability of the wearing band 20 by the antibacterial and deodorizing effects of copper ions, thereby leading to a further enhanced effect of physical therapy by low-frequency stimulation.

The pile yarn 23 may be rubbed by an iron brush to raise a nap on the surface thereof. The nap fills the spaces between the pieces of pile yarn, leading to enhanced conductivity.

Figure 7:
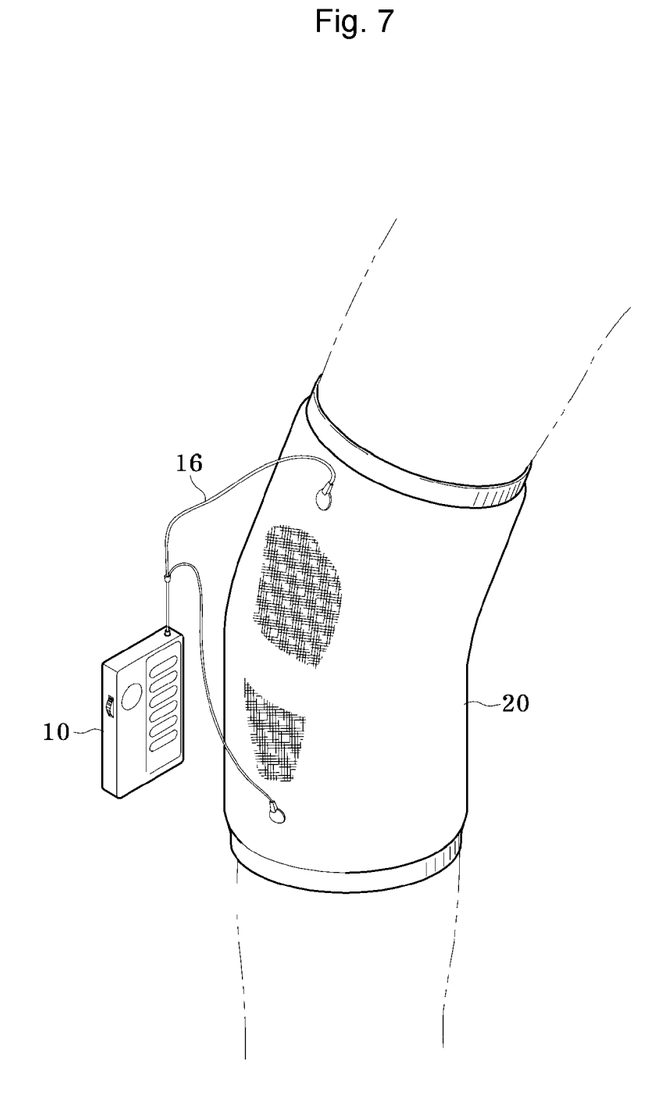
FIG. 7 is a view illustrating a state of a low-frequency therapy wearing band being worn on an arm according to the present invention.

As illustrated in FIG. 7, according to the present invention, the low-frequency therapy wearing band 20 may easily be worn on the wearer's affected part and may come in tight contact with the skin thanks to the elasticity of the band. Therefore, the problems with the conventional art, such as, the bothering process of attaching an adhesive pad or a deterioration of adhesivity, and a resultant reduced massage effect, by repeated use may be addressed, and a more competitive, high-quality, and high-functionality low-frequency therapy device may be implemented.

Figure 8:
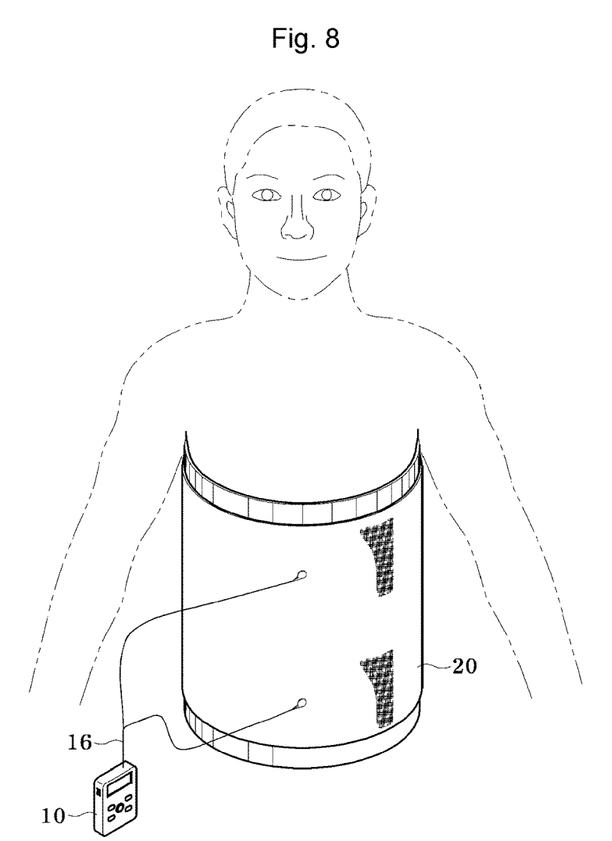
FIG. 8 is a view illustrating a state of a low-frequency therapy wearing band being worn on a back and waist according to the present invention.

As illustrated in FIG. 8, according to the present invention, the low-frequency therapy wearing band 20 may be worn on the affected part very easily and may be worn on a relatively broad body part of the user, such as the back or waist. As such, the low-frequency therapy wearing band 20 has a large area of contact to the human body, allowing for efficient physical therapy.

Figure 9:
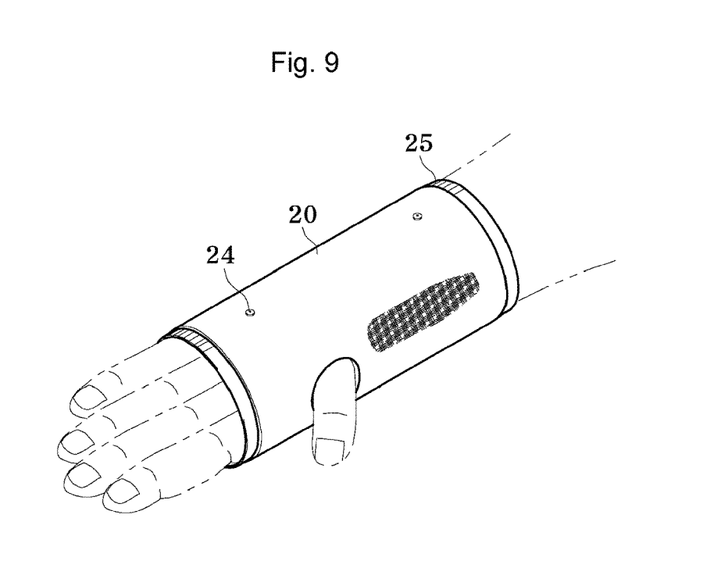
FIG. 9 is a view illustrating a state of a low-frequency therapy wearing hand being worn on a cast according to the present invention.

As illustrated in FIG. 9, the wearing band 20 may be worn on a part that is to be in a plaster cast as if a stocking is. Therefore, the wearing band 20 may be worn quickly and easily while protecting the broken part of the user. A plaster cast may then be worn on the wearing band 20. The wearing band 20 worn under the plaster cast includes the pile yarn that is formed of a conductive fiber, preventing static electricity and providing antibacterial and sterilizing effects.

Further, if physical therapy is conducted low-frequency stimulation, even with the plaster case worn, after the broken bone is hardened to some degree, the stiff muscles may be relaxed, and blood circulation may be promoted. Therefore, no remedial exercise is required after wearing a plaster case, or the period for a remedial exercise may be reduced.

Figure 10:
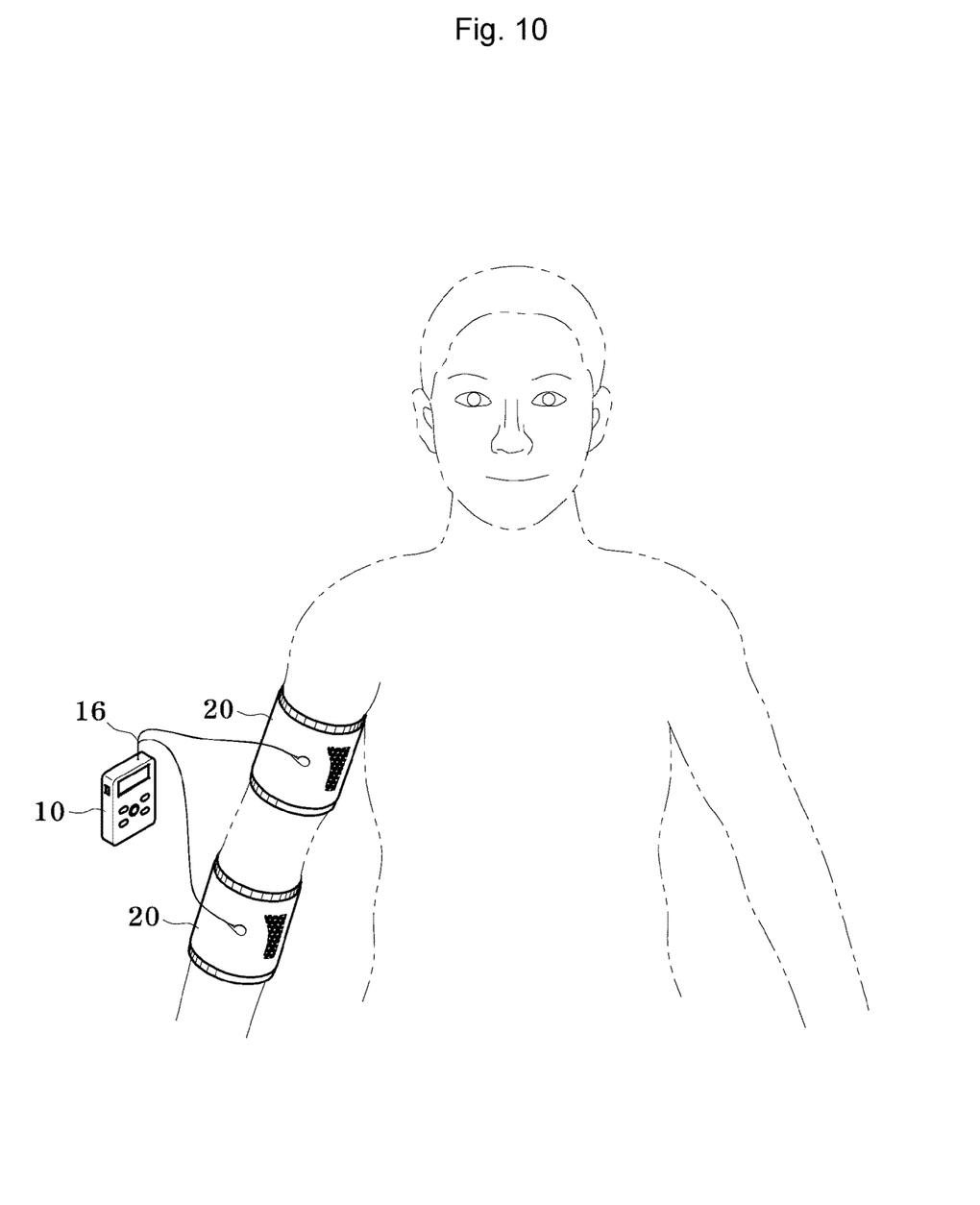
FIG. 10 is a view illustrating a low-frequency therapy wearing band being worn on an according to another embodiment of the present invention.
Figure 11:
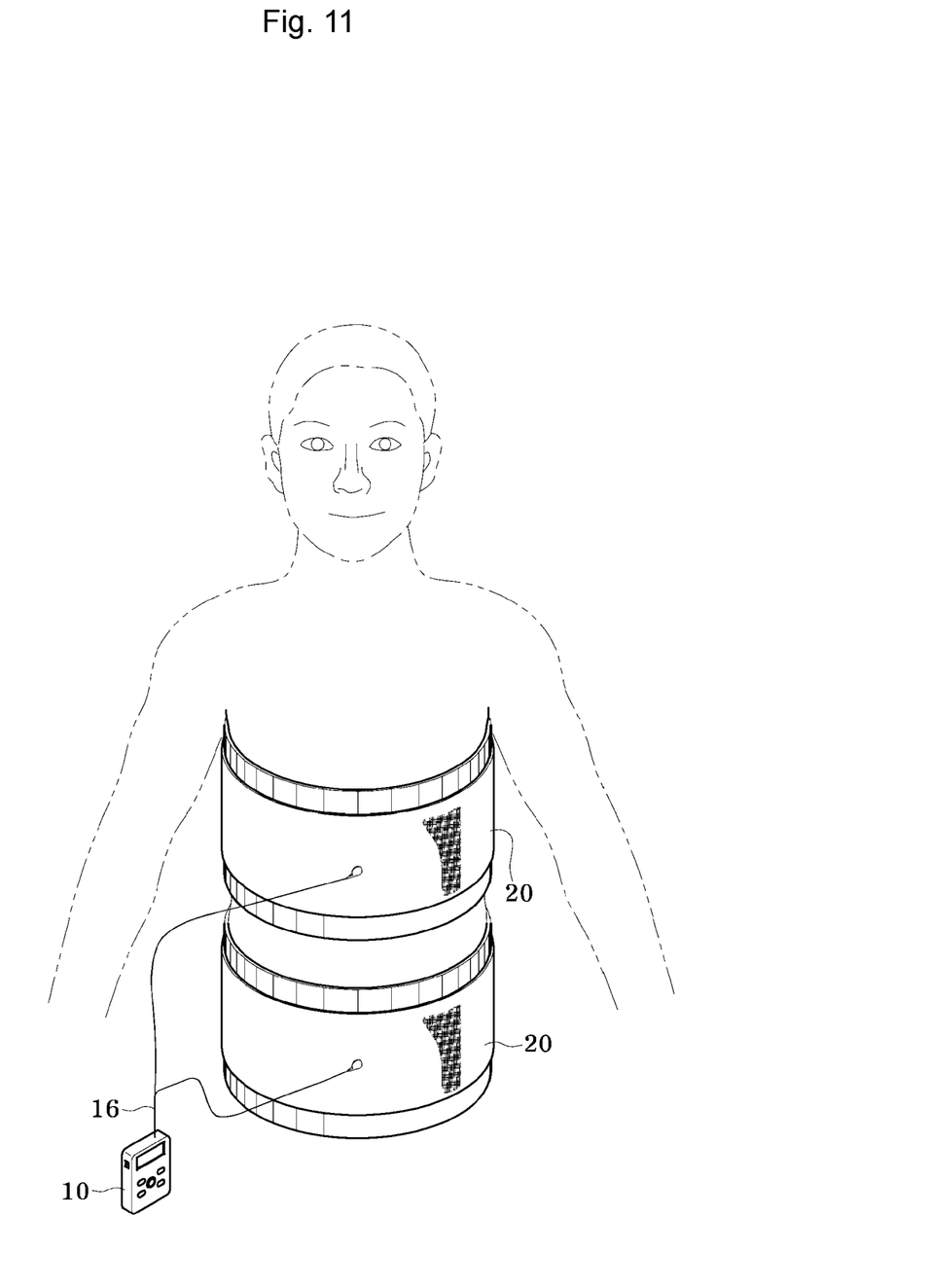
FIG. 11 is a view illustrating a low-frequency therapy wearing band being worn on a back and waist according to another embodiment of the, present invention.

As illustrated in FIGS. 10 and 11, a pair of wearing; bands 20 which are divided from each other may be provided to be simultaneously worn on multiple body parts. Here, a positive current may be transmitted to the upper wearing band, and a negative current may be transmitted to the lower wearing band.

As such, low-frequency stimulation may simultaneously be applied with the pair of wearing bands 20 worn on the multiple body parts, and thus, physical therapy may flexibly be conducted on a broad area.

INDUSTRIAL APPLICABILITY

According to the present invention, a low-frequency therapy wearing band may be formed of a high-quality, high-functionality band that is brought in tight contact with the skin by elasticity. Thus, the wearing band may be worn easily in a broad area of skin so that a broad area of contact to the skin may be secured and efficient physical therapy may be performed. Therefore, the wearing band may contribute to the recovery of motor skills and the raising of self-standability.

What is claimed is:

1. A low-frequency therapy wearing band 20 allowing a low-frequency therapy device 10 including a control box 11 constituted of a case, a power supply 12, a controller 13, a low-frequency wave output unit 14, and a control switch 15 to be connected thereto to provide a low-frequency stimulus to a body part of a wearer to enable physical therapy, the wearing band 20 comprising outer yarn 21 shaped as a cylinder by continuously knitting fiber yarn loops and knitted with fiber yarn, inner yarn 22 knitted with covering yarn, and pile yarn 23 formed of a conductive fiber, knitted at inner surfaces of the inner yarn 22, and applying a low-frequency stimulus while tightly contacting a skin, wherein a cable 16 of the low-frequency therapy device 10 is connected to electrode terminals 24 protruding from a surface to transmit a negative low-frequency current and a positive low-frequency current to the pile yarn 23, and wherein a stainless fiber 30 is knitted on an outside of the outer yarn 21 to prevent static electricity that occurs due to a contact to the wearing band 20.

2. The low-frequency therapy wearing band of claim 1, wherein the pile yarn 23 is any one of a conductive fiber rendered to have conductivity by having copper sulfate react with an acrylic fiber, a conductive fiber obtained by mixing carbon black, which is a conductive material, with a fiber, and a conductive fiber rendered to have conductivity by depositing a metal on a surface of a fiber.

3. The low-frequency therapy wearing band of claim 1, wherein each inner yarn includes metallic copper yarn 221 as a core material and a covering yarn formed by winding coat yarn 222 formed of nylon or polyester around the copper yarn 221, and wherein the copper yarn 221 is heated that receives a current as a cable 16 of the low-frequency therapy device 10 is connected to the electrode terminals 24 of the wearing band 20.

4. The low-frequency therapy wearing band of claim 3, wherein the inner yarn 22 is knitted in the form of a mesh (web) to provide an effect of pile yarn knitting.

5. The low-frequency therapy wearing band of claim 3, wherein a Teflon resin is coated on an outside of the coat yarn 222 to prevent a direct contact to the wearer's skin.

6. The low-frequency therapy wearing band of claim 1, wherein elastic bands 25 are formed at an upper part and lower part of the wearing band 20, and wherein the elastic bands 25 are formed by knitting a synthetic fiber along with rubber yarn.

7. The low-frequency therapy wearing band of claim 1, wherein the wearing band 20 includes a pair of wearing bands that are divided from each other and are simultaneously worn on a plurality of body parts.

8. A low-frequency therapy wearing band allowing a low-frequency therapy device 10 including a control box 11 constituted of a case, a power supply 12, a controller 13, a low-frequency wave output unit 14, and a control switch 15 to be connected thereto to provide a low-frequency stimulus to a body part of a wearer to enable physical therapy, the wearing band 20 comprising outer yarn 21 shaped as a cylinder by continuously knitting fiber yarn loops and knitted with fiber yarn, inner yarn 22 knitted with covering yarn, and pile yarn 23 formed of a conductive fiber, knitted at inner surfaces of the inner yarn 22, and applying a low-frequency stimulus while tightly contacting a skin, wherein a cable 16 of the low-frequency therapy device 10 is connected to electrode terminals 24 protruding from a surface to transmit a negative low-frequency current and a positive low-frequency current to the pile yarn 23, and wherein a surface of any one of the inner yarn 22 and the pile yarn 23 is rubbed by an iron brush to raise a nap on the surface.

\* \* \* \* \*